(12) United States Patent
Williamson (10) Patent No.: US 6,849,852 B2
(45) Date of Patent: Feb. 1, 2005

(54) SYSTEM AND METHOD FOR MONITORING CHANGES IN STATE OF MATTER WITH TERAHERTZ RADIATION

(75) Inventor: Steven L. Williamson, Ann Arbor, MI (US)

(73) Assignee: Picometrix, Inc., Ann Arbor, MI (US)

( * ) Notice: Subject to any disclaimer, the term of this patent is extended or adjusted under 35 U.S.C. 154(b) by 47 days.

(21) Appl. No.: 10/169,303

(22) PCT Filed: Dec. 28, 2000

(86) PCT No.: PCT/US00/35550
§ 371 (c)(1),
(2), (4) Date: Oct. 29, 2002

(87) PCT Pub. No.: WO01/48457
PCT Pub. Date: Jul. 5, 2001

(65) Prior Publication Data
US 2003/0226969 A1 Dec. 11, 2003

Related U.S. Application Data
(60) Provisional application No. 60/173,225, filed on Dec. 28, 1999.

(51) Int. Cl.[7] .................................................. G02B 6/26
(52) U.S. Cl. ..................................... 250/341.6; 250/330
(58) Field of Search ............................... 250/341.6, 330, 250/332, 334, 338.1, 338.4, 358.1, 359.1, 493.1; 372/96

(56) References Cited

U.S. PATENT DOCUMENTS

| | | | | | |
|---|---|---|---|---|---|
| 5,420,595 A | * | 5/1995 | Zhang et al. | ................ | 342/368 |
| 5,623,145 A | * | 4/1997 | Nuss | ........................... | 250/330 |
| 5,663,639 A | * | 9/1997 | Brown et al. | ................. | 324/96 |
| 5,710,430 A | * | 1/1998 | Nuss | ........................ | 250/358.1 |
| 5,729,017 A | * | 3/1998 | Brener et al. | ............. | 250/338.1 |
| 5,894,124 A | * | 4/1999 | Iwabuchi et al. | ........... | 250/310 |
| 5,920,588 A | * | 7/1999 | Watanabe | ..................... | 372/96 |
| 6,078,047 A | * | 6/2000 | Mittleman et al. | ........ | 250/338.1 |
| 6,320,191 B1 | * | 11/2001 | Rudd | ....................... | 250/341.1 |
| 2001/0038074 A1 | * | 11/2001 | Zhang et al. | ............. | 250/341.8 |

FOREIGN PATENT DOCUMENTS

| | | | |
|---|---|---|---|
| EP | 0 841 548 A2 | 5/1998 | |
| WO | WO 99/49297 | 9/1999 | |
| WO | WO 01/38929 A1 | * 5/2001 | ............. G02F/1/01 |

OTHER PUBLICATIONS

New Dimensions in T–Ray Imaging XP–000774572—S. Hunsche; D. Mittleman; M. Kock; and M. Nuss—IEICE Trans. Electron, vol. E81–C. Feb. 1998.

THz Imaging via Electro–Optic Effect—Z. Jiang, X. Zhang—1999 IEEE MTTS Digest.

* cited by examiner

Primary Examiner—Constantine Hannaher
Assistant Examiner—Otilia Gabor
(74) Attorney, Agent, or Firm—Brinks Hofer Gilson & Lione (57) ABSTRACT

A system and method for using terahertz radiation to detect and monitor a substance undergoing a change in phase from a liquid phase to a solid phase or vice-versa is disclosed. By employing terahertz radiation in either the pulsed mode or in the continuous-wave (CW) mode, the system can non-invasively monitor these changes. The system uses the principle that matter in a liquid state will absorb and attenuate terahertz radiation to a larger degree than matter in a semisolid or solid state. Most terahertz radiation absorption occurs due to the rotational motions of molecules, i.e. either whole molecules or groups of atoms rotating about molecular bonds.

31 Claims, 8 Drawing Sheets

SYSTEM AND METHOD FOR MONITORING CHANGES IN STATE OF MATTER WITH TERAHERTZ RADIATION

CROSS-REFERENCE TO RELATED APPLICATIONS

This application is a filing under 35 U.S.C. 371, which claims priority to International Application Ser. No. PCT/US00/35550, filed Dec. 28, 2000, which claims the benefit of U.S. Provisional Application No. 60/173,225, filed Dec. 28, 1999.

FIELD OF INVENTION

The present invention relates to a terahertz (THz) radiation detection and analysis system. More specifically, the present invention relates to a terahertz radiation detection and analysis system and method used to detect phase changes in matter.

BACKGROUND

Presently there is no commercially available device or method to non-invasively or non-destructively monitor phase changes in substances, such as adhesives or glue as they cure or dry. Furthermore, there are no known devices or methods that can monitor adhesive curing when the adhesive is sandwiched between two adjoined parts, such as two pieces of paper, two sheets of plastic, layers in laminated wood or ceramics, or glass.

Accordingly, there is a need in the art to monitor the processing of such a curing procedure to insure the integrity of an adhesive bond and to monitor the quality of various products.

SUMMARY OF THE INVENTION

Terahertz radiation (electromagnetic radiation in the range of 50 GHz to 10 THz) both pulsed and continuous-wave, can be used for this purpose. Terahertz radiation will be absorbed and attenuated differently when it passes through matter in a liquid state, semisolid state, or solid state. These attenuation differences can be detected and monitored to detect the state of a sample in the process of changing phase such as an adhesive undergoing a curing process.

The invention comprises an apparatus and method, using terahertz radiation, that allows the detection and monitoring of many different materials as they change from the liquid phase to the solid phase or vice-versa. By employing terahertz radiation in either the pulsed mode or in the continuous-wave (CW) mode, a system can non-invasively monitor these changes. The terahertz system of the present invention uses the principle that matter in a liquid state will absorb and attenuate terahertz radiation to a larger degree than matter in a semisolid or solid state. Most terahertz radiation absorption occurs due to the rotational motions of molecules, i.e. either whole molecules or groups of atoms rotating about molecular bonds. THz radiation is more highly absorbed by more polar rotating moieties. Rotational motion occurs readily when a material is in the liquid state, however, as a material hardens or freezes, this kind of motion is substantially restricted, thus making the material more transparent to terahertz radiation. Most liquid adhesives are highly polar, providing a strong contrast between the absorption of the freely rotating liquid adhesive molecules and the cured adhesive whose molecules cannot rotate.

The same physical properties which allow terahertz radiation to be used to monitor the curing of glue, i.e. the transition from a liquid state to a solid state, also allow terahertz radiation to be used to monitor other liquid-solid or solid-liquid phase changes such as water to ice and vice-versa. This is true for ice or for frozen objects such as frozen food containing water. Furthermore, terahertz radiation may be used to monitor the amount of water in moisture critical commercial products such as powdered drinks and baby food.

The advantage of the terahertz monitoring system is its versatility and ease of use in an industrial environment. The terahertz system of the present invention is ruggedly packaged and can be used in an industrial environment for the processing of the aforementioned common commercial products such as epoxy, glue, ice cubes, baby food, and frozen food, but is not limited to such. The terahertz system may be used to monitor the curing of adhesive used to couple materials such as cardboard, laminated sheets of wood or plastic, caulking, silicone sealant, and other types of adhesives. Furthermore, the terahertz system may also be used to monitor the drying of paints, such as on a car body.

By taking advantage of the varying absorption properties of terahertz radiation, with respect to phase changes in matter, a terahertz device can be employed to monitor these types of phase changes.

Further objects, features and advantages of the invention will become apparent from a consideration of the following description and the appended claims when taken in connection with the accompanying drawings.

DETAILED DESCRIPTION OF THE PREFERRED EMBODIMENT

Figure 1:
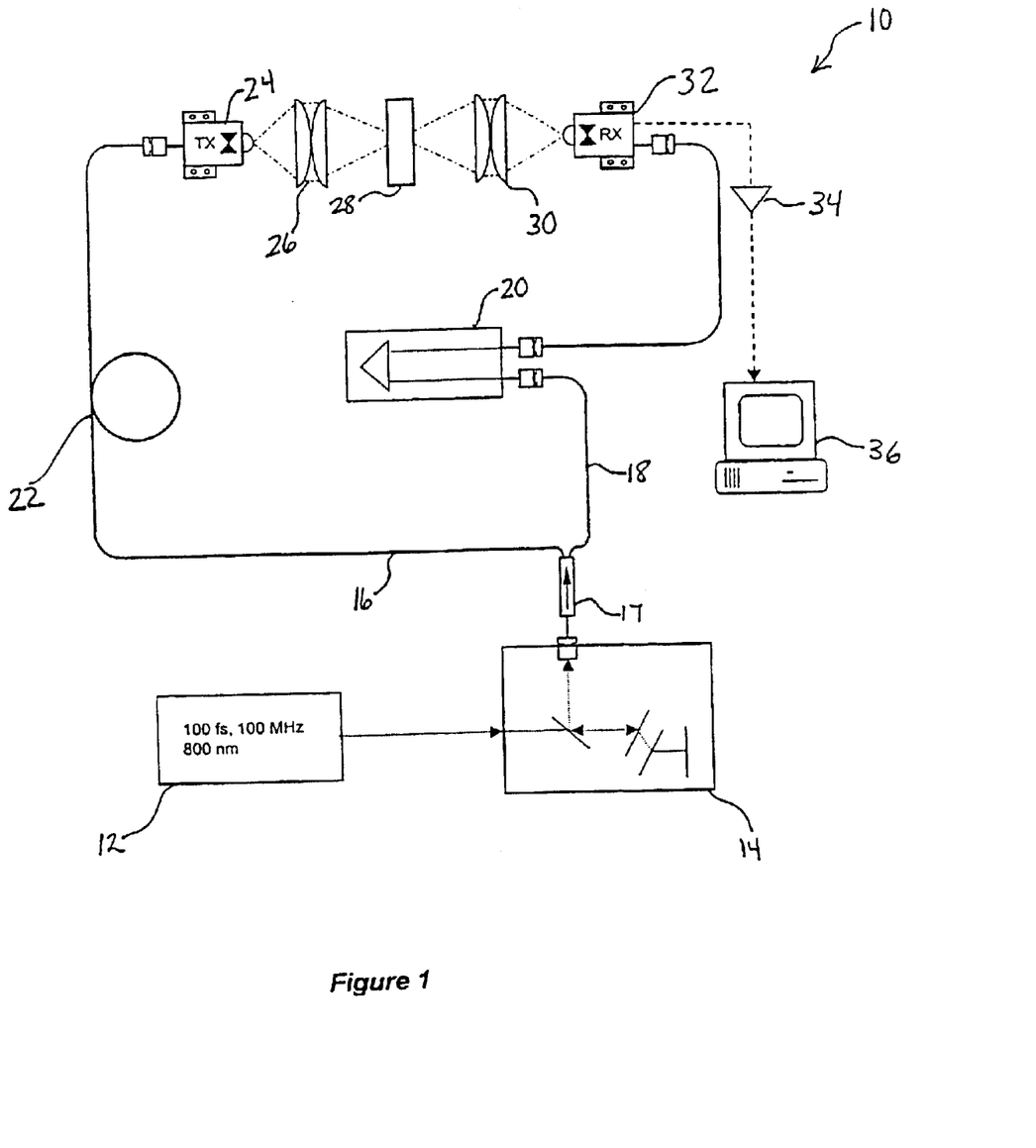
FIG. 1 is a diagrammatic view of a time domain terahertz system of the present invention.

FIG. 1 is a diagrammatic view of a terahertz electromagnetic radiation emission and detection system shown generally as 10. An optical source 12 comprising a Ti:sapphire laser producing sub-100 femtosecond pulses at 800 nm is coupled to a precompensator 14. Although a Ti:sapphire laser is the preferred optical source 12, other short pulse sources may be used such as: a modelocked Er-doped fiber laser frequency doubled to produce pulses at 750–800 nm; a colliding-pulse modelocked (CPM) laser; an amplified Ti:sapphire laser consisting of a seed pulse that is amplified to higher energies; a frequency-doubled, modelocked Nd based glass laser; a modelocked laser based on any of the chromium doped hosts: LiCaF, LiSrAlF, or LiSrGaAlF; or any laser source producing femtosecond output pulses at megahertz repetition rates, but is not limited to such. Although the preferred embodiment uses a laser source operating at around 800 nm, a source such as an Er doped fiber laser, operating at 1550 nm may be used if the appropriate semi-conductor material is also used in the transmitter and receiver.

In operation, the output pulse from the optical source 12 is split by a fiber splitter 17 to single mode optical fibers 16 and 18. In order to achieve a transform-limited pulse at the output of the single mode optical fibers 16 and 18, a precompensator 14 is used to add dispersion of a sign opposite to the dispersion acquired in the fibers 16 and 18. Dispersion is the name given to the property of group velocity variation with wavelength. This will tend to spread, stretch, and/or distort an optical pulse shape, making it indistinct. The simplest form of dispersion comes from the propagation of light through bulk material. The source of this dispersion is the non-linear frequency-dependent index of refraction. The precompensator 14 may be comprised of gratings, holographic gratings, prisms, grisms, Bragg-fiber gratings, Gires-Tourmier interferometer, or any other combination thereof that results in a negative group velocity dispersion system. The optical fibers 16 and 18 can comprise numerous commercially available single mode fibers.

As the optical pulse exits the optical fiber 16 it will travel through a fiber optic delivery apparatus 22 to strike a terahertz transmitter 24, which will emit a single-cycle or half-cycle of electromagnetic radiation in the terahertz frequency range. The preferred embodiment of the terahertz transmitter 24 employs a photoconductive element, generating electron-hole pairs and an impulse electrical current. The photoconductive element may be a pn-junction diode, pin photodiode, metal-semiconductor-metal photodiode, point-contact photodiode, heterojunction photodiode, or a simple semiconductor, which can be fabricated with any semiconductor element comprised of low temperature grown GaAs, semi-insulating-GaAs, Silicon (crystalline or ion-implanted) on Sapphire, InAs, InP, InGaAs, or any other photo active element but is not limited to such. The photo conductive element used to generate a terahertz pulse can also be of the kind outlined in U.S. Pat. No. 5,420,595 entitled "Microwave Radiation Source" which issued to Hang et al. On May 30, 1995, and is incorporated by reference herein.

A current pulse will be generated by the optical pulse striking the photo conductive element of the terahertz transmitter 24. The variation in current will generate electromagnetic radiation in the terahertz frequency range. The temporal shape of the electromagnetic radiation is determined both by the shortness of the input optical pulse and the metal antenna structure that is coupled to the photo conductive element. In the preferred embodiment the antenna is in a dipole configuration. The antenna configuration for this preferred embodiment is outlined in U.S. Pat. No. 5,729,017, "Terahertz Generator and Detector", which issued to Brenner et al. On May 17, 1998, and is incorporated by reference herein. The radiation in the preferred mode will be from 50 gigahertz to 100 terahertz, but any electromagnetic frequency above or below this preferred range is possible.

The terahertz radiation is transmitted through optical elements 26 which condition the terahertz radiation. The conditioned terahertz radiation then passes through a sample 28 and a second optical element 30 to a terahertz receiver module 32. As discussed previously, phase changes in the sample 28 can be characterized by a frequency-dependent absorption, dispersion, and reflection of terahertz transients in signals which pass through the sample 28. By monitoring the total energy of the received terahertz radiation passing through the sample 28, material phase changes may be monitored. The terahertz radiation receiver 32 in FIG. 1 is configured to detect electromagnetic radiation in the terahertz range, after the terahertz radiation has passed through the sample 28. The terahertz radiation receiver 32 can be placed at any position surrounding a sample 28, so as to detect absorbed, reflected, refracted or scattered radiation. The terahertz radiation receiver 32 will then generate an electrical signal proportional to the power or energy of the received terahertz radiation which is subsequently amplified by amplifier 34 and interpreted, scaled, and/or digitized by a data acquisition system 36.

The terahetz receiver 32 is synchronized to the terahertz transmitter 24 by optical pulses traveling through optical fiber 18 and fiber optic delay 20 controlled by a trigger device (not shown). The fiber optic delay 20 will control the gating of the received terahertz signal.

The system described herein represents the preferred embodiment used to perform the demonstration. However, a pulsed, time-domain system could be based on electron-optic generators and other detectors could be used as well. Other embodiments would consist of all electronic methods with Gunn diodes or non-linear transmission lines as transmitters and balometers as detectors.

Figure 2:
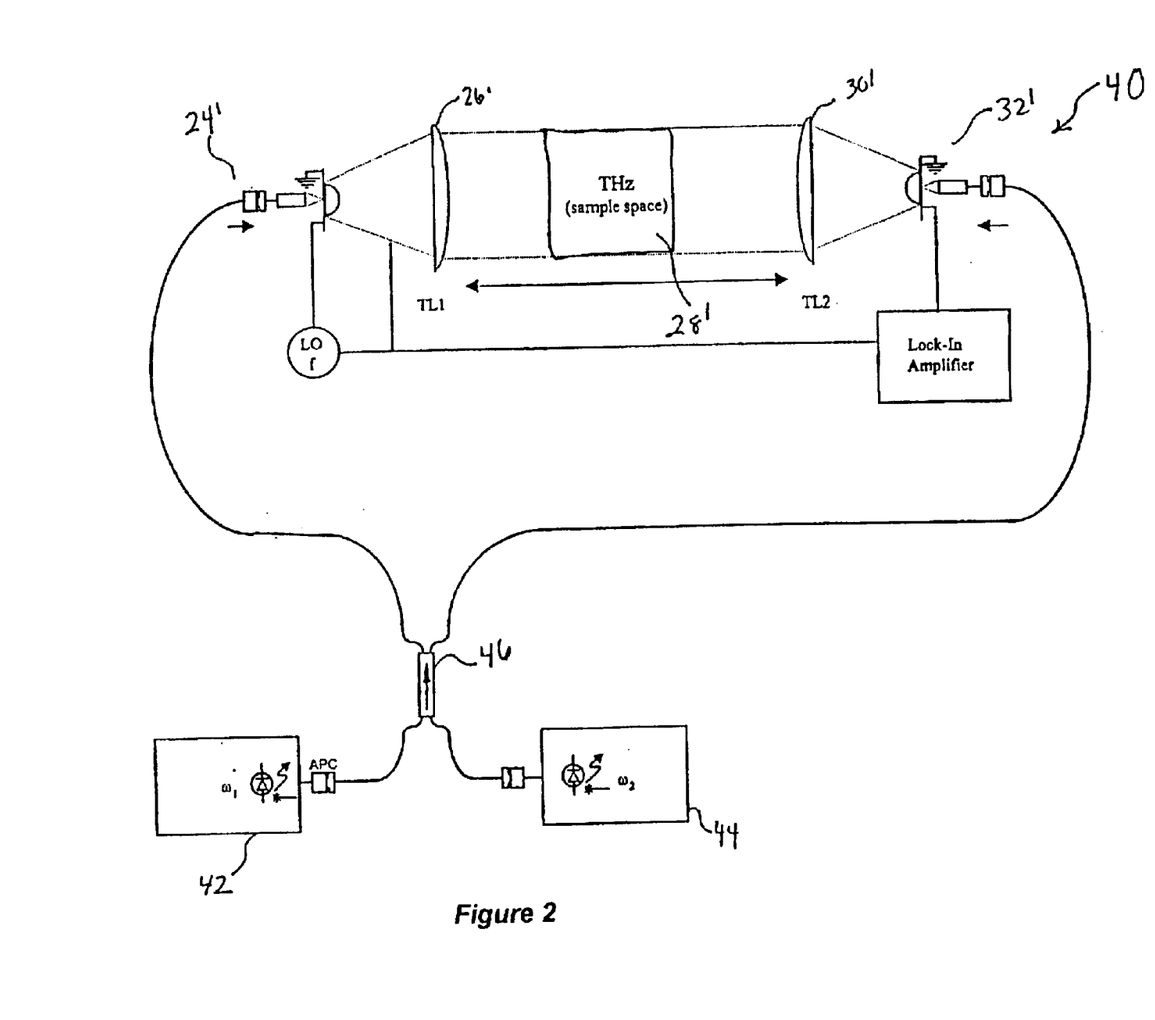
FIG. 2 is a diagrammatic view of a continuous wave terahertz system of the present invention.

FIG. 2 is a diagrammatic figure of an alternate terahetz transmitting and receiving system utilizing a continuous wave system. Two semiconductor diode lasers 42 and 44 are optically coupled to produce a continuous wave signal at optical coupling point 46. The continuous wave signal is generated by the constructive and destructive interference of the diode laser 42 and 44 outputs. The laser 42 and 44 may be modulated to generate any desired frequency. Similar to the first embodiment of the present invention shown in FIG. 1, the continuous wave is applied to a terahertz transmitter 24' that generates terahertz radiation. The terahertz radiation is transmitted through optical elements 26' which condition the terahertz radiation. The conditioned terahertz radiation then passes through a sample 28', a second optical element 30', and a terahertz receiver module 32'. The signal from the terahertz receiver 32' is analyzed similar to the first embodiment. The continuous terahertz radiation generated by the system 40 will enable measurements that are wavelength sensitive, such as the monitoring of a gaseous material with a sharp absorption line. The continuous wave system configuration, of this preferred embodiment, is outlined in further detail in U.S. Pat. No. 5,663,639, "Apparatus and Method for Optical Heterodyne Conversion", which issued to Brown, et al. On Sep. 2, 1997, and is incorporated herein by reference.

Figure 3:
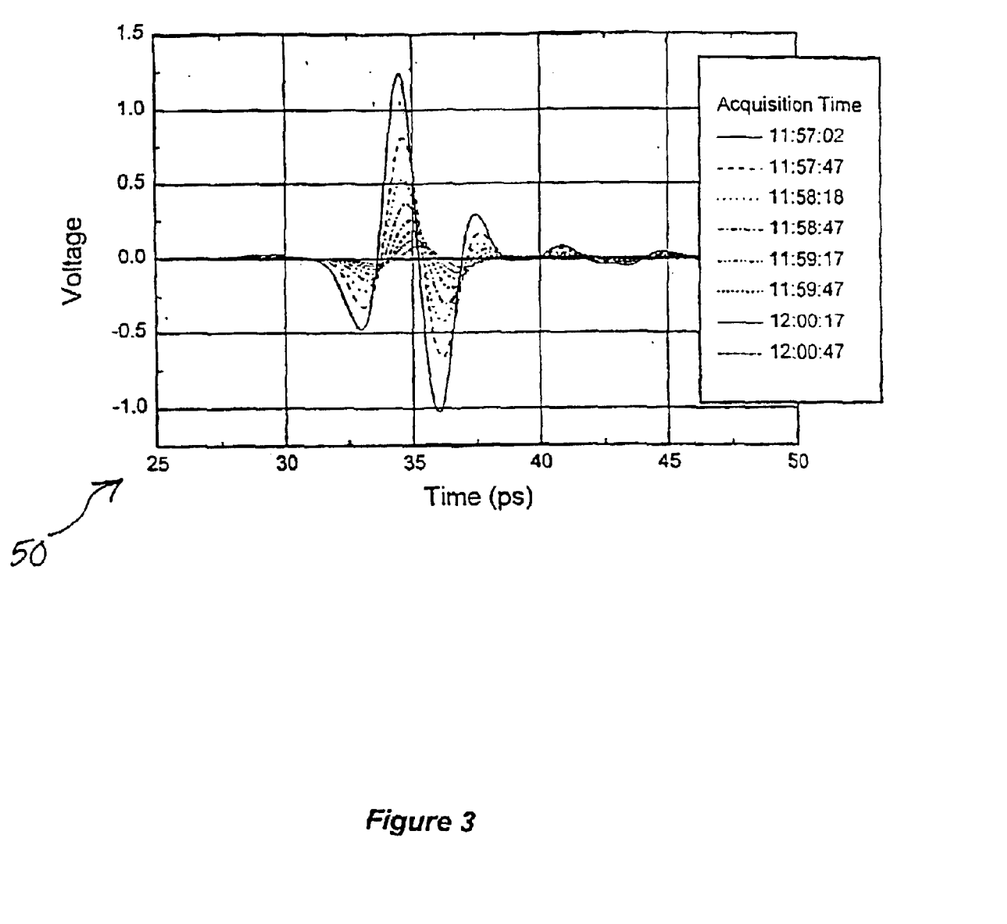
FIGS. 3 and 3a are graphs illustrating the absorption of terahertz radiation for melting ice.
Figure 3A:
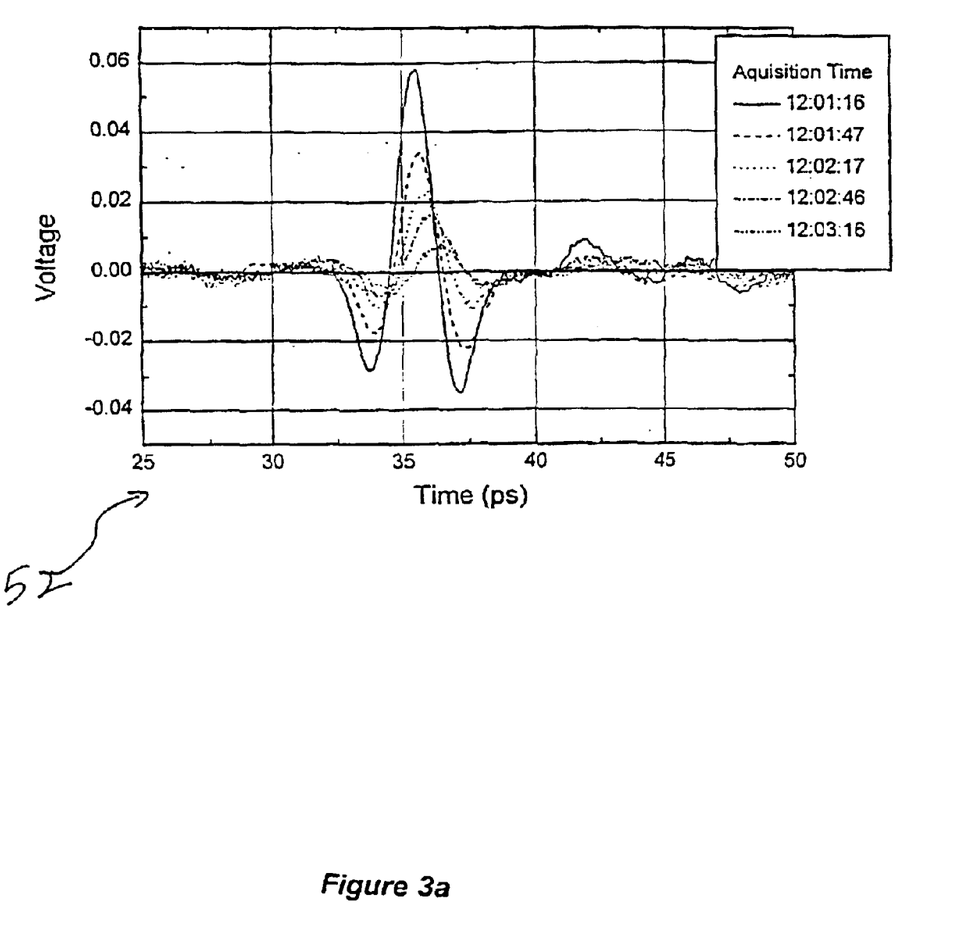

FIGS. 3 and 3a are illustrations of pulsed waveforms transmitted through a cube of ice as the cube of ice slowly melts over time. The graphs 50 and 52 illustrate the amplified voltage signal of the terahertz receiver 32 versus time. As can be seen, the transmitted power, as measured by the voltage signal, from the terahertz radiation passing through the ice slowly decreases as the water in the beam path starts to increase.

Figure 4:
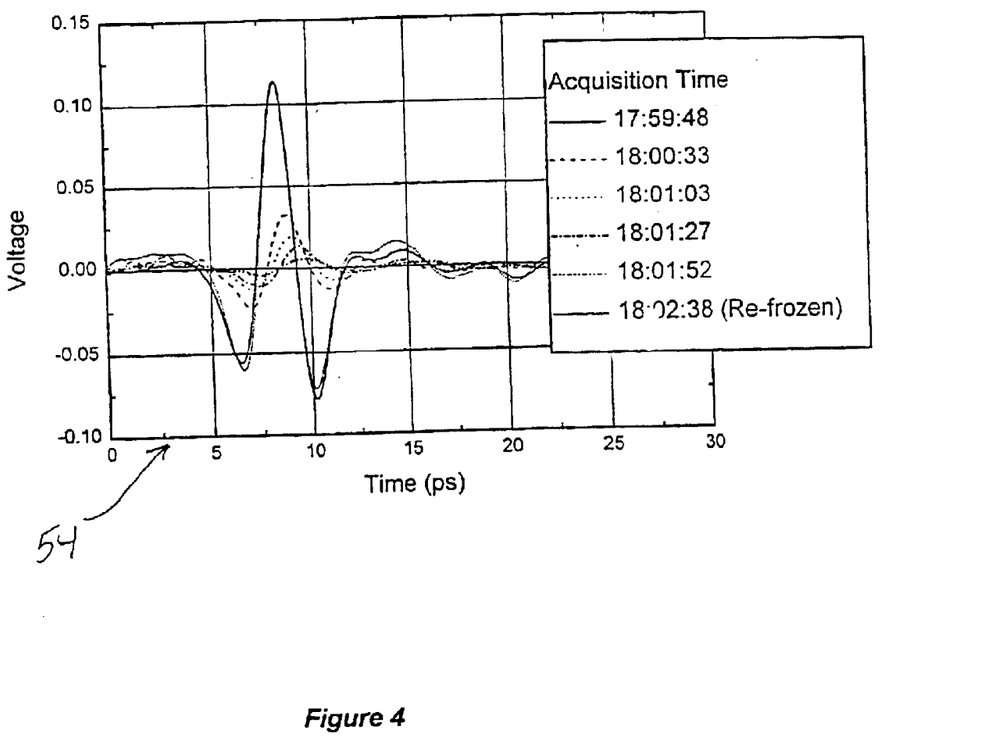
FIG. 4 is a graph illustrating the absorption of terahertz radiation for a frozen cucumber that has been melted and then re-frozen.

FIG. 4 shows a series of pulsed waveforms taken as a frozen cucumber slice starts to melt, and then again after it has been re-frozen. The graph 54 illustrates the amplified voltage signal of the terahertz receiver 32 versus time. Similar to FIGS. 3 and 3a the water content of the frozen cucumber determines the attenuation of the terahertz radiation.

Figure 5:
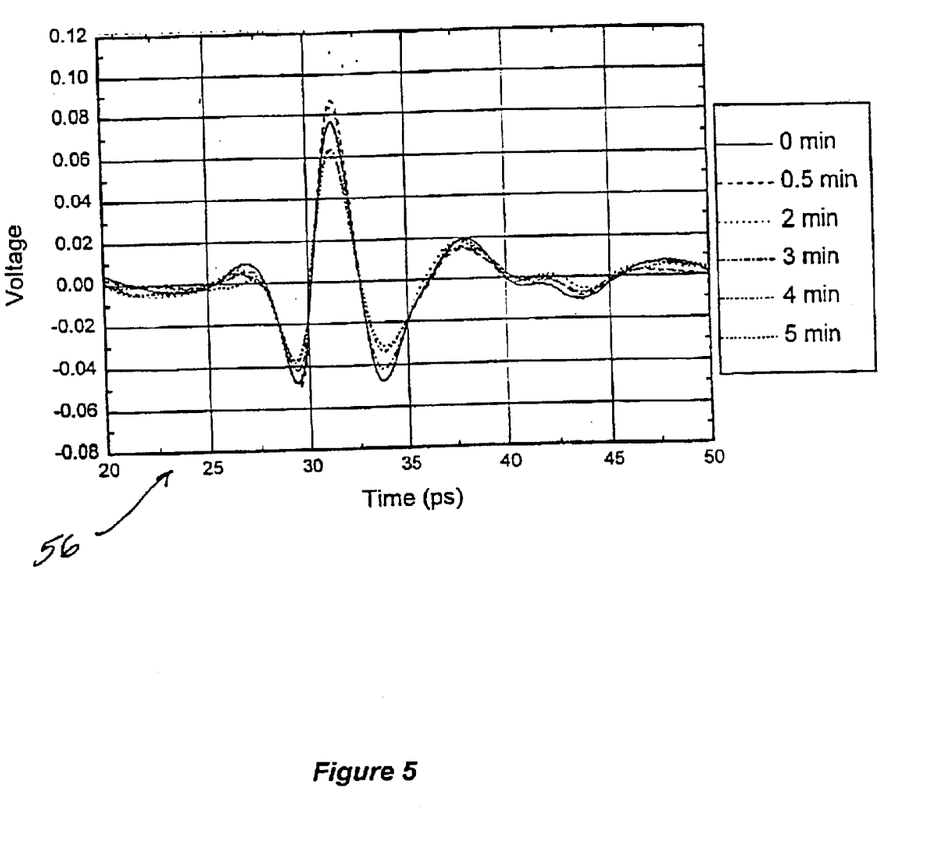
FIGS. 5, 5a, and 5b are graphs illustrating the absorption of terahertz radiation for curing epoxy.
Figure 5A:
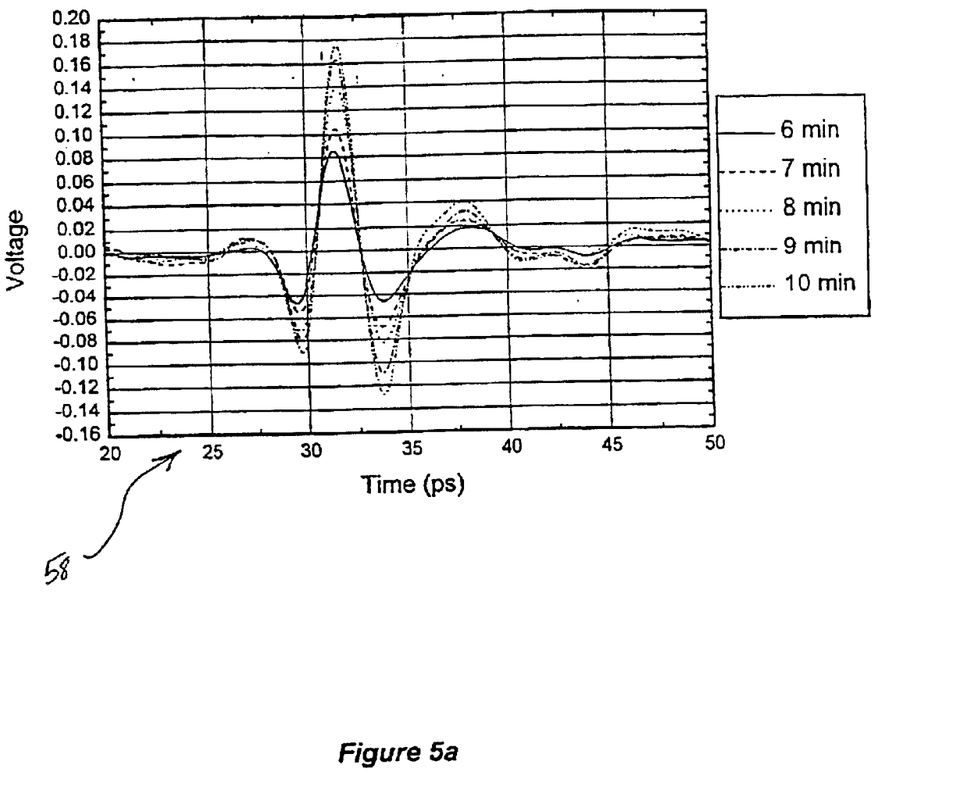
Figure 5B:
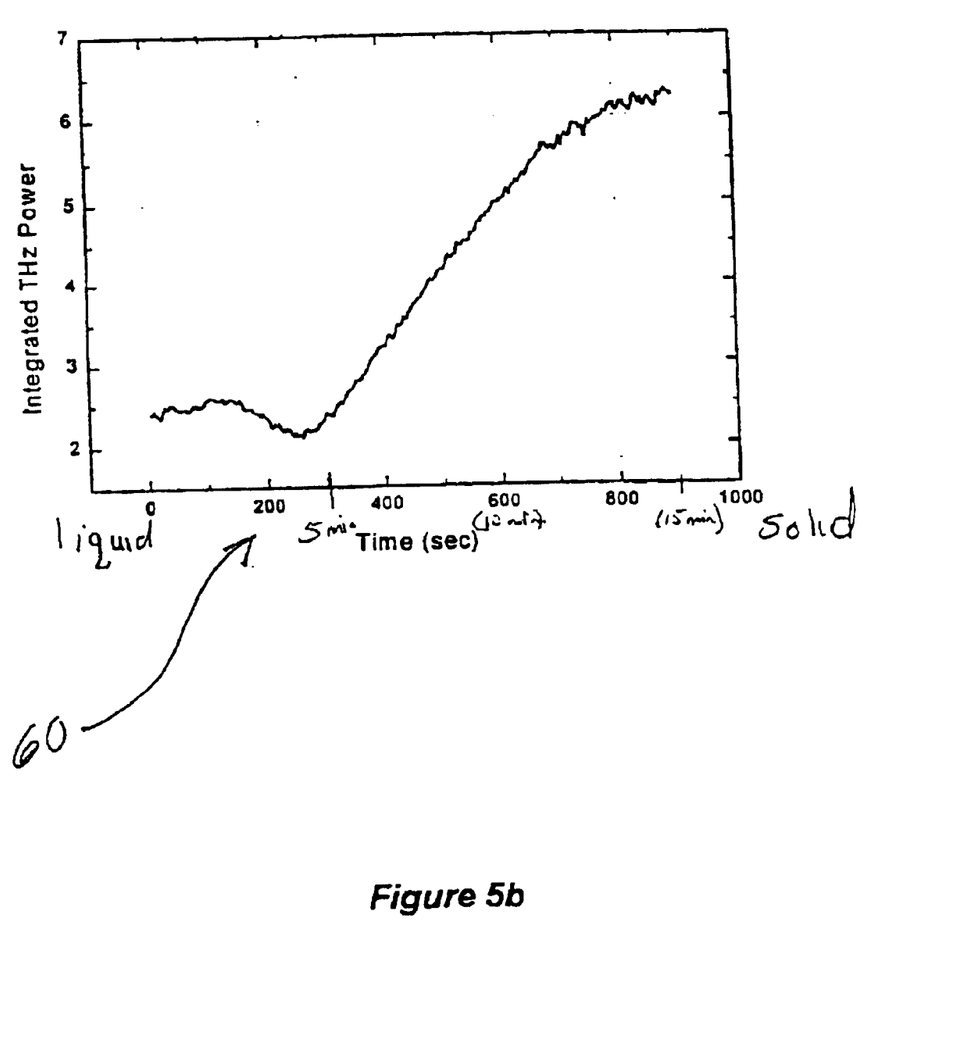

FIGS. 5, 5a, and 5b show a series of waveforms taken as standard, two-part, five-minute epoxy cures. The graphs 56 and 58 illustrate the amplified voltage signal of the terahertz receiver versus time and the graph 60 illustrates the integrated terahertz power as detected versus time. Since the epoxy is curing, i.e. going from a liquid state to a solid state, this signal voltage is increasing in strength over time.

Graphs 56 and 58 were taken during an experiment that continuously monitored the total energy transmitted through a 1 cm path length of epoxy as it cured. Both FIGS. 5 and 5a show the same energy trend for the epoxy, during the first 5 minutes of curing. The graphs 56 and 58 show about the same transparency to terahertz radiation with a slight decrease occurring at 4–5 minutes after mixing, this dip is followed by a steady rise in transmitted energy over the next 10 minutes.

With specific reference to FIG. 5b, an example of an application of terahertz radiation to monitor liquid to solid phase changes in glues, epoxies, water, and other similar material is illustrated. Graph 60 shows the transmitted terahertz power through a cuvette of standard 2-part, 5 minute epoxy. As the epoxy starts to polymerize, the cuvette of epoxy becomes more transparent to the terahertz radiation, as indicated by the increase in transmitted terhertz power over time. Initially, as the two parts are mixing, the cuvette of epoxy appears to become temporarily more opaque (transmitted terahertz power decreases), just before the solidification begins.

Since, the phase transition from liquid to solid and the freezing of rotational vibrations in most substances are usually detectable in the terahertz regime, there is good reason to believe that a similar result would be found for other glues.

The graphs 50, 52, 54, 56, 58, and 60 were taken using a pulsed or time-domain terahertz system. In the preferred embodiment of the present invention, a continuous wave (CW) Terahertz system like that shown in FIG. 2 will be used in industrial applications. This system would constantly monitor the total transmitted power at a specific terahertz frequency, rather than intermittently monitor terahertz radiation over a broad wavelength range.

It is to be understood that the invention is not limited to the exact construction illustrated and described above, but that various changes and modifications may be made without departing from the spirit and scope of the invention as defined in the following claims.

What is claimed is:

1. A system for determining whether a sample under inspection is undergoing a change in state, the system comprising:
    a laser light source for generating laser light;
    an optically-driven terahertz transmitter which converts the laser light into
    terahertz electromagnetic radiation, wherein the terahertz electromagnetic
    radiation is transmitted through the sample;
    an optically-driven terahertz receiver positioned opposite the terahertz transmitter for receiving the terahertz electromagnetic radiation transmitted through the sample; and
    an analyzer for comparing the terahertz electromagnetic radiation transmitted by the optically-driven terahertz transmitter to the terahertz electromagnetic radiation received by optically-driven terahertz receiver to determine whether the sample is undergoing a change in state.

2. The system of claim 1 wherein the analyzer further compares a transmitted power of the terahertz electromagnetic radiation transmitted by the optically-driven terahertz transmitter to a received power of the terahertz electromagnetic radiation received by the optically-driven terahertz receiver to determine whether the sample is undergoing a change in state.

3. The system of claim 1 wherein the analyzer further compares a transmitted peak voltage amplitude of the terahertz electromagnetic radiation transmitted by the optically-driven terahertz transmitter to a received peak voltage amplitude of the terahertz electromagnetic radiation received by the optically-driven terahertz receiver determine whether the sample is undergoing a change in state.

4. The system of claim 1, wherein the laser light source is a laser capable of producing an optical pulse having a duration of approximately 100 femtoseconds.

5. The system of claim 4, wherein a fiber delivery system is used to deliver the optical pulse from the laser light source to the optically-driven terahertz transmitter and receiver.

6. The system of claim 5, further comprising a precompensator for adding dispersion to cancel dispersion acquired in the fiber delivery system.

7. The system of claim 1, wherein the laser light source further comprises a plurality of single-frequency light sources for generating a plurality of single frequency-light signals, wherein the plurality of single frequency-light signals are added coherently at the optically-driven terahertz transmitter and receiver.

8. The system of claim 7, further comprising a fiber combiner for spatially overlapping the plurality of single frequency-light signals.

9. The system of claim 1, wherein the terahertz transmitter and receiver further comprise a photo conductive element for converting the laser light to the terahertz electromagnetic radiation.

10. The system of claim 9, wherein the photo conductive element is a low-temperature-grown GaAs semiconductor.

11. The system of claim 1, wherein the terahertz transmitter and receiver further comprise an electron-optic element for converting the laser light to the terahertz electromagnetic radiation.

12. The system of claim 11, wherein the electron-optic element is comprised of ZnTe.

13. The system of claim 1, wherein the terahertz transmitter and receiver further comprise an antenna for improving coupling efficiency of the terahertz electromagnetic radiation out of the transmitter and into the receiver.

14. The system of claim 1, further comprising an optical delay device for introducing a delay in the transmission of the laser light from the laser light source to the optically-driven terahertz receiver.

15. The system of claim 1, further comprising a terahertz optical element in alignment with the terahertz transmitter for focusing the terahertz electromagnetic radiation onto the sample.

16. The system of claim 1, further comprising a terahertz optical element in alignment with the terahertz receiver for concentrating the terahertz electromagnetic radiation onto the terahertz receiver.

17. A method for determining whether a sample under inspection is undergoing a change in state, the method comprising:
    generating a coherent lightwave using a laser light source;
    converting the coherent lightwave into terahertz electromagnetic radiation using an optically-driven terahertz transmitter, wherein the optically-driven terahertz transmitter transmits the terahertz electromagnetic radiation through the sample;
    receiving the terahertz electromagnetic radiation transmitted through the sample using an optically-driven terahertz receiver positioned opposite the optically-driven terahertz transmitter; and
    comparing the transmitted terahertz electromagnetic radiation to the received terahertz electromagnetic radiation to determine whether the sample is undergoing a change in state.

18. The method of claim 17, wherein comparing the transmitted terahertz electromagnetic radiation to the received terahertz electromagnetic radiation further comprises comparing a transmitted power of the terahertz electromagnetic radiation transmitted by the optically-driven terahertz transmitter to a received power of the terahertz electromagnetic radiation received by the optically-driven terahertz receiver for determining whether the sample is undergoing a change in state.

19. The method of claim 17, wherein comparing the transmitted terahertz electromagnetic radiation to the received terahertz electromagnetic radiation further comprises comparing a transmitted peak voltage amplitude of the terahertz electromagnetic radiation transmitted by the optically-driven terahertz transmitter to a received peak voltage amplitude of the terahertz electromagnetic radiation received by the optically-driven terahertz receiver for determining whether the sample is undergoing a change in state.

20. The method of claim 17, further comprising producing an optical pulse having a duration of approximately 100 femtoseconds.

21. The method of claim 20, further comprising delivering the optical pulse to the optically-driven terahertz transmitter and receiver using a fiber optic delivery system.

22. The method of claim 21, further comprising adding dispersion using a precompensator to cancel dispersion acquired in the optical delivery system.

23. The method of claim 17, further comprising improving coupling efficiency of the terahertz electromagnetic radiation out of the optically-driven terahertz transmitter and into the optically-driven terahertz receiver using an antenna, wherein each the transmitter and receiver include the antenna.

24. The method of claim 17, further comprising focusing the terahertz electromagnetic radiation onto the sample using a terahertz optical element in alignment with the optically-driven terahertz transmitter.

25. The method of claim 17, further comprising focusing the terahertz electromagnetic radiation transmitted through the sample onto the optically-driven terahertz receiver using a terahertz optical element in alignment with the terahertz receiver.

26. The method of claim 17, wherein generating a coherent lightwave using a laser light source further comprises generating a plurality of single frequency-light signals using a plurality of single frequency-light sources, wherein the plurality of single frequency-light signals are added coherently at the optically-driven terahertz transmitter and receiver.

27. A system for determining whether a sample under inspection is undergoing a change in state, the system comprising:

a pulsed laser light source for generating a pulse of laser light;

an optically-driven terahertz transmitter which converts the laser light into a pulse of terahertz electromagnetic radiation, wherein the terahertz electromagnetic radiation is transmitted through the sample;

an optically-driven terahertz receiver positioned opposite the terahertz transmitter for receiving the terahertz electromagnetic radiation transmitted through the sample;

a fiber delivery system for transmitting the laser light from the laser light source to the optically-driven terahertz transmitter and receiver;

an optical delay device for introducing a delay in the transmission of the laser light from the laser light source to the optically-driven terahertz receiver; and an analyzer for comparing the terahertz electromagnetic radiation transmitted by the optically-driven terahertz transmitter to the terahertz electromagnetic radiation received by the optically-driven terahertz receiver to determine whether the sample is undergoing a change in state.

28. The system of claim 27, wherein the laser light source is a laser capable of producing an optical pulse having a duration of approximately 100 femtoseconds.

29. The system of claim 27, further comprising a precompensator for adding dispersion to cancel dispersion acquired in the fiber delivery system.

30. The system of claim 27 wherein the analyzer further compares a transmitted power of the terahertz electromagnetic radiation transmitted by the optically-driven terahertz transmitter to a received power of the terahertz electromagnetic radiation received by the optically-driven terahertz receiver to determine whether the sample is undergoing a change in state.

31. The system of claim 27 wherein the analyzer further compares a transmitted peak voltage amplitude of the terahertz electromagnetic radiation transmitted by the optically-driven terahertz transmitter to a received peak voltage amplitude of the terahertz electromagnetic radiation received by the optically-driven terahertz receiver determine whether the sample is undergoing a change in state.

* * * * *

UNITED STATES PATENT AND TRADEMARK OFFICE
CERTIFICATE OF CORRECTION

PATENT NO. : 6,849,852 B2
DATED : February 1, 2005
INVENTOR(S) : Steven L. Willliamson It is certified that error appears in the above-identified patent and that said Letters Patent is hereby corrected as shown below:

Column 5,
Line 47, after "into", delete paragraph break;
Line 49, after "electromagnetic", delete paragraph break.

Column 6,
Lines 32 and 35, delete "electron-optic" and substitute -- electro-optic -- in its place.

Column 8,
Line 7, after "into", delete paragraph break;
Line 9, after "terahertz", delete paragraph break .

Signed and Sealed this

Twenty-third Day of August, 2005

JON W. DUDAS
*Director of the United States Patent and Trademark Office*